US007255885B2

(12) United States Patent
Lee

(10) Patent No.: US 7,255,885 B2
(45) Date of Patent: Aug. 14, 2007

(54) PREPARATION OF CHINESE HERBAL COMPOSITE RECIPE USED IN HORTICULTURE

(76) Inventor: Chien-Yung Lee, 2F, No. 60, Shouhua Rd., Gangshan Jen, Kaohsiung Hsien (TW)

( * ) Notice: Subject to any disclaimer, the term of this patent is extended or adjusted under 35 U.S.C. 154(b) by 379 days.

(21) Appl. No.: 10/858,056

(22) Filed: Jun. 2, 2004

(65) Prior Publication Data

US 2005/0158403 A1 Jul. 21, 2005

(30) Foreign Application Priority Data

Jan. 20, 2004 (CN) ........................ 2004 1 0033482

(51) Int. Cl.
*A61K 36/483* (2006.01)
*A61K 36/489* (2006.01)
*A61K 36/886* (2006.01)
*A61K 36/904* (2006.01)

(52) U.S. Cl. ....................... 424/725; 424/405; 424/744

(58) Field of Classification Search ..................... None
See application file for complete search history.

(56) References Cited

U.S. PATENT DOCUMENTS 4,735,935 A * 4/1988 McAnalley .................. 514/53
5,908,628 A * 6/1999 Hou ........................... 424/735
2004/0086580 A1* 5/2004 Tripp et al. ................. 424/745

FOREIGN PATENT DOCUMENTS

CN 1081617 A * 2/1994
CN 1284361 A * 2/2001

OTHER PUBLICATIONS

Hall et al. (Journal of Pharmaceutical Sciences (1983), vol. 72, No. 11, pp. 1282-1284.*
Homan (Drug Preparation and Extraction (2002); Royal Pharmaceutical Society of Great Britain).*

* cited by examiner

*Primary Examiner*—Susan Coe Hoffman
(74) *Attorney, Agent, or Firm*—Bacon & Thomas, PLLC

(57) ABSTRACT

A recipe of Chinese herbal composite used in horticulture to kill pests. The practical applications of this recipe include pest killing, germ and virus eradication of vegetables, fruit trees, flowers and economical plants. This recipe is composed of *Gleditisia Sinensis, Sophora flavescens, Aloe vera, Stemona tuberosa, Brucea javanica* and *Dioscorea collettis* vice versa. We prepare it with modern principles and scientific methods to emulsion spray. Those so called modern and scientific are the emulsion processes, micronization, permeability and the multiply potency it possessed. Several laboratory and field test proved that this invention had definite effect on the past killing, germ eradiation and virus inhibition. This invention is belongs to non toxic Chinese herbal preparation. The spray does not harm or cause toxic effect as it touch human skin, eyes, nasal mucosa, lip, mouth and tongue. It does not accumulate in human body and pollute environment.

8 Claims, No Drawings

PREPARATION OF CHINESE HERBAL COMPOSITE RECIPE USED IN HORTICULTURE

BACKGROUND OF THE INVENTION

1. Field of the Invention

The present invention relates generally to medicine, and more particularly to a Chinese herbal composite recipe and its preparation which used in horticulture to kill pests.

2. Description of the Related Art

The progress in material civilization in these 2 or 3 centuries bring many positive values to human beings. At the same time, there are many severe negative effects appear in ecosystem and environment. The population of the world increased and the horticulture and agriculture plants which feed human must increasing production. Therefore, under the negative changes and effects of the ecosystem, such crops must face the disturbance of disease, toxicity and pest and made it to produce difficultly.

The chemical agricultural chemicals propagate, because it's definitely killing effects and easily usage. It becomes the standby of production in farmers and always the most popular in the market. Until the mid of the twentieth centuries, the techniques of test and examination propagate. The senses of environment and pollution arose and proved gradually that such chemical toxins will remain toxin and pollution. They endanger human health and natural environment. The developed countries prohibit their production domestically. From Jan. 1, 2004, the European Allies will stop selling 320 kind of agricultural chemicals officially and import agricultural side products which polluted by such residues. In fact, the entrepreneurs knew that trend early and devote themselves in production and selling of low toxicity agricultural chemicals. They spent many capitals in research and development and the real effects of such low toxic products are far from those and make the resistance of virus and pest easily.

There are many records about agricultural pest killing, germ eradiation and toxin inhibition in the Chinese medical books. The pest killing plants, such as the *Buddleia officinalis, Veratrum mentzeanum, Skimmia japonica, Euphorbia fischeriana* steud, *Sapindus mukorossii* Gaertn, tobacco, *Pyrethrum cineraefolium, Chalcanthite, Stemona tuberosa, Gleditsia sinensis, Melia azedarach* and vice versa. Therefore, the potent Chinese herbs do not according to the specifications of environment protection and sanitation. By the actual experiments, we can kill pests by 6:1 preparations if we can use non toxic Chinese herbs. It shows the conditional situations in economic benefits and usage applications. Therefore, we need some breakthrough in the idea to develop non toxic agricultural chemicals in Chinese herbs.

SUMMARY OF THE INVENTION

The objective of this invention is to provide a Chinese herbal composite recipe used in horticulture plants to kill pests, eradiate germs and in inhibit viruses. The modern and scientific extraction and preparation methods will augment 6 times and more than it's original potency. It will open the new applications and values of Chinese medicine. I hope it can replace synthetic agricultural chemicals and maintain agriculture profit, human health and avoid environment pollution and poisoning.

To achieve the objectives mentioned above of this invention, I supply the transformation mechanism, drug dispensing, drug preparation method, pharmacology description, range and method of application, caution, transformation and interior experiments and preliminarily field experiments.

DETAILED DESCRIPTION OF PREFERRED EMBODIMENTS

The transformation mechanism called in this invention is the mechanism which to achieve more potency. It includes the theories used in traditional Chinese medicine, emulsion and permeability and micronization processes and vice versa.

Under the idea of avoiding poisonous Chinese herbs, the potency of organic Chinese herbs is hard to compete with the synthetic agricultural chemicals and pure chemicals.

However, it's principle of application is different to that of the synthetic agricultural chemicals and pure chemicals. It is not based on poison killing principle but on the theories of traditional Chinese medicine not to harm the body to eradiate germs or killing Ascarid, tape worm, hook worm, Nematode and inhibit poisons to heal the disease.

To increase potency on the original statement, the inventor analyzed the effective components of these drugs especially. To make them have multiply effects in assemble and preparation. I take reasonable concentration extraction to avoid the losses of alkaloids and necessary ingredients. Especially, I take more advanced and scientific grinding and colloid milling machine than original preparation method to perform micronized and special emulsion process.

The effects of pesticide, germicide and toxin inhibition of Chinese herbs is to promote drug entered from the derma and mucosa into the bodies of warms, this is the first step. This will cause the environment inside the body and the tissues change dramatically. To achieve such goals, the most important thing is the micronization of drugs and it's permeability except the composition of drugs and it does multiply effects. Therefore, this preparation uses some emulsion process to make water soluble emulsion because of the water soluble emulsion is easily absorbed by skin and mucosa.

The tension between liquid and gas is called surface tension. The liquids which do not intermingle each other, like the Mosla chinensis oil used in this preparation (the main ingredients are thymol, carvacreol and p-cymene), turpentine oil and the tension between the percolate is called the surface tension. The emulsified agents like yellow gelatin, Tragacantha, gum Arabic are belonging to surface active agents. They can reduce the surface tension between oil and percolate and down to 10 dyne/cm. The objective of emulsion is to make the oily effective ingredients into small droplets by emulsion agents and colloidal mill which supply energy from the outside world. That will make it micronized and more easily penetrate into worm bodies and to increase the absorption rate by derma and mucosa of worms and germs. That will change the interior environ of germs and worms dramatically.

As mentioned above, this is the mechanism of drug achieve effect and multiply potency. To prove this point of mechanism, the inventor performs the interior pest killing experiments (see interior experiment I) of transformation mechanism. That proved the turnover effect with emulsion added.

The Chinese compose recipe spray used in horticulture is prepared by Chinese herbs listed below, then I concentrated extraction and make powder by ratio with some definitely ratio percolate. Then I pulverized it by grinding and sieving with emulsified agents added.

(1) Concentrated Chinese powder and ratio.

*Gleditsia sinensis* 80-120 gm *Stemona tuberosa* 80-120 gm

*Sophora flavescens* 80-120 gm *Brucea iavanica* 80-120 gm

*Aloe vera* 80-120 gm (2) Percolate and ratio.

distilled water 600-800 ml alcohol 150-250 ml glycerin 80-120 ml (3) Emulsified agents used in original 3000ml of solution.

Yellow gelatin or Gum arabic 40-60gm.

Turpentine oil 40-60 ml.

Distilled *Mosla chinensis* oil 30-50 ml.

Preparation (1) Take concentrated Chinese composite recipe 1000 gm then passed milling machine for 2 to 3 times and soak for 2 hours. The first time percolate is 1200 ml. The second percolate is 1000 ml after soaking for 2 hours. Add distilled water 1200 ml and soak for 4 hours then percolate to get the third percolate. Combine these three percolates for later use.

(2) Take yellow gelatin or gum Arabic 50 gm and mix turpentine oil and *Mosla chinensis* oil 50 ml, respectively. Put them into colloid mill for high speed grinding than add distilled water 100 ml. Continue grinding for 3 to 5 minutes and repeat for 3 times.

(3) Adding 50 gm of Mirabilite and 3 gm of benzoic acid. Mixing them with (1) and (2). Passing them in golden mill and grinding 2 to 3 times.

Pharmacology

1. *Gleditsia sinensis*: Pesticide, germicide, toxin inhibition; contain gledinin and alkanes. It will increase permeability with other drugs.
2. *Sophora flavescens*: It has broad spectrum germicide effect and can help other drugs to kill pests.
3. *Aloe vera*: Pesticide, germicide, the lauric acid and myristic acid is helpful for mirabilite to promote solution penetration.
4. *Stemona tuberosa*: Anti-microbe, pesticide, killing flied and mosquito and other 10 or more agricultural pests.
5. *Brucea javanica*: Pesticide. The effect is enhanced by the gledinin and sodium sulfate (Mirabilite).
6. *Dioscorea collettii*: Germicide and pesticide. The important ingredient is saponin unit.
7. *Mosla chinensis*: It is extracted with distilled method. It contains pesticide and germicidal effects of essential oils like carvacrol, thymol and p-cymene. They make this preparation more delicate. I use it as the emulsion oil and make micronized material accomplish the assumed effect.
8. Turpentine oil: Germ resistance, germicide; emulsion oil.
9. Yellow gelatin: Emulsifying agent, protect plants.
10. Mirabilite: Working with other drugs to produce help and multiply effects to increase permeability and achieve pest and bacteria killing effects. (Please see drug description sheet for detail information.)

Range and Method of Application

1. This spray is applicable to economic crops, fruit trees, flowers, vegetables Lima bean. It also applies to general agricultural damages caused by pests, germs and viruses on crops.
2. Take this spray and dilute to certain ratios of water then spray on stems and leaves of crops or pests by manual or mechanical sprayer.
3. Depend on the order and families of pests, germs and viruses and the severity to determinate the dilution ratio.

Dilute 15 to 30 times for every pests, germs and toxins.

Dilute 30 to 60 times need 24 to 48 hours to kill or repel them.

Dilute 60 to 150 times has prevention effect.
4. The preparation is a contact pesticide. It shows eradiation effect on larva, adult and eggs. These pest and diseases can not produce resistance to this preparation. It do not block environ biological chains. You do not have to increase dilution ratio gradually. The prevention period can be extended. It is harmless to animals and human.

Caution

1. This invention is a topically Chinese medicine pest and germ killing agent. It is prohibited to take orally. It may cause gastrointestinal symptoms when take orally. You can purchase rare green bean powder, rare glycyrrhizin powder and talcum powder 6 gm, respectively. Mixing 6 gm of cold water with these things and take it. It will show some laxative effect or you should consult medical assistance.
2. The diluents of this preparation are harmless to animals and human. It do not cause any harm as contact with skin, eyes, nose, mouth and tongue.
3. This preparation should store in cool and dry places to prevent deterioration caused by high temperature.

Addendum

1. This horticultural Chinese composite spray is a quantitized concentrated Chinese extract powder. It is prepared by certain ingredients and ratio of percolate then dissolved in special emulsified agents.
2. This invention is the best practice of the Chinese composite recipe shown above. It can produce sufficient effect without adding *Aloe*. On the other side, the extraction of this recipe all using *Dioscorea collettii* powder as adjuvant but other drugs will do, too.
3. The feature of this preparation's re-extraction percolate is composed of the following ration of liquids.
4. Distilled water 60-80%, alcohol 15-25 % and glycerin 8-12 %.
5. The feature of this preparation is the emulsion process. It adds yellow gelatin
6. The other feature of this invention is adding 30 to 120 gm of Mirabilite (sodium sulfate) in to 3000 ml of original solution.
7. The feature of this preparation retains the right as application of environmental sanitation. That is to say, this invention and feature of preparation can be sprayed on the living environment to keep the sanitation of environ.

Drug Description Datasheet

| NO: 1 | | | |
|---|---|---|---|
| Name | Zaolia | Official name | *Gleditsia sinensis* |
| Dependence | China Pharmacopoeia Volume IV pp 480 (China Sheng-Ghai scientific technology publication) | | |
| Growing district, collect season, parts | Grow in northeast, north south of China and Si-chuan, Qui-zhou province. Collect fruits and dry as they ripen and darken in autumn. | | |
| Preparation, extraction process, method | (1) Take 12 kg of *Gleditsia sinensis* and soak in water for 6 hours. Collect percolate for 2 times then evaporate the residue water to get 5 liters of fluid extract. Adding 2 kg *Dioscorea collettii* of powder and stir well. Drying it in 45° C. then pulverized by passing #120 sieve to make fine powder. Collect and store them for later use. | | |

-continued

| NO: 1 | |
|---|---|
| Effective ingredient | The capsules contain tri-terpene saponin that is gledinin saponin. Its basic saponin unit is gledinin, gledinin saponin, wax alcohol, novacosane, nor-septacosane, stigmasterol, sitosterol and tannin. |
| Original recorded pharmacological effects | Germicide effect. The *Gleditsia sinensis* extract show fungus inhibition effect on *T. violaceum* and *Norcardis asteroids* in skin. *Fructus Gleditsiae abnormalis* can kill larva of nematode and show hemolysis in vitro. The main feature is local mucosa stimulation effect. In central system, it can cause them convulsion and paralysis then death with breathe exhaustion. |
| Pharmacological applications, purposes | Pesticide and germicide objectives are achieved by the ingredients contain in the *Gleditsia sinensis* such as saponins, alkanes and alcohols. They can cooperate with other drugs to promote penetration effect. |

| NO: 2 | | | |
|---|---|---|---|
| Name | Kushen | Official name | *Sophora flavescens* Ait |
| Dependence | China Pharmacopoeia Volume IV pp 634 (China Sheng-Ghai scientific technology publication) | | |
| Growing district, collect season, parts | Grow in everywhere in China. Take all plants in September to October and remove the upper part, base of stem and fibrous roots. Cut fibrous roots into single strand. Wash out dirt then dry or bake it. | | |
| Preparation, extraction process, method | Take 12 kg of *Sophora flavescens* and soak in water for 3 hours. Collect percolate for 2 times then evaporate the residue water to get 5 liters of fluid extract. Adding 2 kg *Dioscorea collettii* of powder and stir well. Drying it in 60° C. then pulverized by passing #120 sieve to make fine powder. Collect and store them for later use. | | |
| Effective ingredient | The roots contain 13 alkaloids including matrine and many flavonoids mixtures. Otherwise, the roots contain tri-terpene saponin, soy saponin and kurarinone. | | |
| Original recorded pharmacological effects | The in vitro experiments show that 1% matrine has apparent bacteria inhibition effects on Shigella, *E. Coli*, Proteus, *B-streptococcus* and *Staphylococcus aureaus*. The total flavones of *Sophora flavescens* and their ethanol extract have killing or growth inhibition effects on *Giardia lamblia* Stiles in vitro. | | |
| Pharmacological applications, purposes | It can use specific alkaloids and saponins to achieve goals of killing pests and bacteria. The inventor observed 20 concentrated Chinese medicine drugs powder all using starch as adjuvant for 20 years and found that the *Sophora flavescens* did not eat into by worms and not change its quality. The package still remains intact. It shows the effect of germicide. | | |

| NO: 3 | | | |
|---|---|---|---|
| Name | Luhui | Official name | *Aloe vera* L. var chinensis |
| Dependence | China Pharmacopoeia Volume VIII pp 51 (China Sheng-Ghai scientific technology publication) | | |

-continued

| NO: 3 | |
|---|---|
| Growing district, collect season, parts | Grow in Fu-jiann, Taiwan, Kuang-tong, Si-chuan, Yun-nan. Gather the middle and lower parts of leaves by batches separately. Cut the leaves open and collect liquids then drying it. The other way is to cut it and add the same part of water then boiling for 2 to 3 hours. Filtering, concentrating and drying. |
| Preparation, extraction process, method | Purchase pure and clean Aloe concentrate blocks in the market. Pulverized before use. |
| Effective ingredient | The leaves contain 11 acids such as Alesin, Aloe tannin, lauric acid, myristic acid and vice versa. There are some polysaccharides and sugar polymers. |
| Original recorded pharmacological effects | Pesticide, germicide. |
| Pharmacological applications, purposes | Lauric acid and the sodium sulfate in the Mirabilite can cooperative together to increase penetration ability into worm body. |

| NO: 4 | | | |
|---|---|---|---|
| Name | Baibu | Official name | *Stemona tuberose* Lour |
| Dependence | China Pharmacopoeia Volume VIII pp 189 (China Sheng-Ghai scientific technology publication) | | |
| Growing district, collect season, parts | *Stemona tuberose* grows in southeast province of China, Hu-nan, Hu-peh and Si-chuan. Collect them after 3 years of planting. Remove tubers after wilting of upper parts of shoot before spring. Remove fine roots and boiling in hot water to well done then drying or baking them. | | |
| Preparation, extraction process, method | Take 12 kg of *Sophora flavescens and soak in* water for 3 hours. Collect percolate for 2 times then evaporate the residue water to get 5 liters of fluid extract. Adding 2 kg *Dioscorea collettii* of powder and stir well. Drying it in 60° C. then pulverized by passing #120 sieve to make fine powder. Collect and store them for later use. | | |
| Effective ingredient | The *Stemona tuberose* contains 13 alkaloids including syemonine, tuberostemonine and isotuberostemonine. It also contains sugar, fats, proteins, ash and 6 different acids including oxalic acid. | | |
| Original recorded pharmacological effects | 1. Anti-microbe.<br>2. Anti-parasite: In vitro tests show that 50% solution can kill pin worm in 20 hours. The tuberostemonine can paralyze Ascarid.<br>3. Insect killing effects: The *Stemona tuberose* water solution and alcohol solution has effects on lice and cause eggs of lice not hatch. It also show contact killing effect on 10 or more pests including maggot, larva of mosquito, bed bug, aphids, larva of *Chilo simples* and spider. | | |
| Pharmacological applications, purposes | Pesticide, germicide and anti-viral effects. | | |

| NO: 5 | | | |
|---|---|---|---|
| Name | Yadanzi | Official name | *Brucea jananica* |
| Dependence | China Pharmacopoeia Volume V pp7 (China Sheng-Ghai scientific technology publication) | | |
| Growing district, collect season, parts | Grow mainly in Fu-kien, Taiwan, Hai-nan, Kwang-dong, Kwang-si, Yun-nan and Kwei-chow. The fruits ripen in autumn. Collect fruits as the skin of fruits darken then cleaning and drying. | | |

-continued

| NO: 5 | |
|---|---|
| Preparation, extraction process, method | Take 12 kg of *Brucea jananica* and soak in water for 6 hours. Collect percolate for 2 times then evaporate the residue water to get 5 liters of fluid extract. Adding 2 kg *Dioscorea collettii* of powder and stir well. Drying it in 45° C. then pulverized by passing #120 sieve to make fine powder. Collect and store them for later use. |
| Effective ingredient | It contains more than 30 ingredients which structural similar to bitter ingredients of quassin. There are several glycosides including lignan of *Hemerocallis fulva*, vanillic acid and *Hypericum*. It also contains oleic acid, triglyceride and oil of *Brucea jananica*. |
| Original recorded pharmacological effects | Anti-malaria and kill plasmodium and amoeba. The crude extract can repel nematodes and tape worms in large intestine. It also has repelling effects on pin worm and Ascarid. |
| Pharmacological applications, purposes | It shows multiply effects with *Mirabilite* and *Gleditisia sinensis* and demonstrates the features pesticide effect. |

| NO: 6 | |
|---|---|
| Name | Beixie    Official name    *Discorea collettii* Hook |
| Dependence | China Pharmacopoeia Volume VIII pp 231 (China Sheng-Ghai scientific technology publication) |
| Growing district, collect season, parts | Grow mainly in Che-kiang, Anh-wei, Jiang-si, Hu-nan. Digging the root stem in autumn and winter then remove the fibrous roots. Cleaning the dirt and slice for druying. |
| Preparation, extraction process, method | Take 10 kg of *Discorea collettii* and pulverized by passing #100 sieves to make fine powder as the adjuvant of collecting fluid extracts. |
| Effective ingredient | It contains 9 steroids. Dios - genin, Yamogenin, Δ 3,5-deoxy-tigogenin, Δ3,5-deoxy-neotigogenin, Diosgenin palmitate, Yamogenin palmitate, β-Sitoterol, a pair of Epimerides and two tzi-gan. |
| Original recorded pharmacological effects | The water extract has insect killing effects. It shows effective ingredients is *discorea saponin*. It has anti-fungal effect to Trichophyton and *Giardia lamblia* but no effect to bacteria. The *Dioscorea collettii* has the effect of fish poison but not apparently as tested. |
| Pharmacological applications, purposes | Pesticide and as adjuvant. |

Drug Description Datasheet

| NO: 7 | |
|---|---|
| Name | Howgining    Official name    *Mosla chinensis* Maxim. |
| Dependence | China Pharmacopoeia Volume VII pp 91 (China Shang-Ghai scientific technology publication) |
| Growing district, collect season, parts | It grows in east China, Taiwan, Kwei-chow. The flowers bloom in autumn and winter. Collect it as the stems and leaves prosper. Drying under shade and pack into small bundles. |
| Preparation, extraction process, method | Take 12 kg of *Mosla chinensis* and chop into fine stripes. Place them into distillation barrel and press firmly. Using heat to perform partial distillation in order to get the essential oil about 240 ml. Remove the remainder and store the essential oil in the bottle for later use. |

-continued

| NO: 7 | |
|---|---|
| Effective ingredient | The *Mosla chinensis* is called the Shi-xiang-ru. The total plant contains volatile oil 2% including carvacrol 71.64%, p-cymene 10.10%, p-isopropyl phenyl methyl alcohol 5%, β-pinene 1.52%, terpineol 1.23%, thymol 1.40%, caryophyllene 1.36%, β-farnesene 0.25%, limonene 0.15%. |
| Original recorded pharmacological effects | The *Mosla chinensis* volatile oil possesses stronger broad spectrum germicide effect. The main effective anti-bacterial ingredients are thymol, carvacrol and p-cymene. |
| Pharmacological applications, purposes | Used as emulsifying oil. It can potentiate the pesticide, germicide potency of essential oils and bring other pest and germ killing agents' potency. |

| NO: 8 Emulsifying oil | |
|---|---|
| Name | Songlievou    Official name    Pinus oil |
| Dependence | China Pharmacopoeia Volume II pp 305 (China Shang-Ghai scientific technology publication) |
| Growing district, collect season, parts | It grows mainly in Kwang-dong and other provinces. We get the volatile oils distilled or extracted from the oily resin. |
| Preparation, extraction process, method | Purchase authentic pure and clean turpentine for later use. |
| Effective ingredient | It contains resin acids, fatty acids, mono-terpines and semi-terpines |
| Original recorded pharmacological effects | 1. Anti-microbe effect. In vitro experiments show stronger anti-fungal effects (*Candida albicans*) on *Tinea corporis* and dermatophytosis It has certain degree of germ inhibition effects on *Staphylococcus aureaus* and *E. Coli*. It is used ad emulsifying oil in this preparation. |
| Pharmacological applications, purposes | Emulsifying agent, germicide and parasite repelling. |

| NO: 9 Emulsifying agent | |
|---|---|
| Name | Yellow gelatin    Official name    *Colla corii Bon's* |
| Dependence | China Pharmacopoeia Volume IX pp 680 (China Sheng-Ghai scientific technology publication) |
| Growing district, collect season, parts | Chop dried yellow ox leather into small cubes. Adding them into water and soak for 2 days. You must change water and stirring well frequently. Cleaning it as the leather soften and put into copper pot. Boiling it gently with 5 times of water. Adding water frequently and filtering supernatant for every 24 hours. Repeat these for 3 times. Precipitate the supernatant with alunite and pour the supernatant. Re-heat and condense in the copper pot till the liquid do not absorb by filtering paper. Adding some yellow wine or candy sugar to collect the gelatin. Pour it into the plate and cool. Chop it into small pieces for drying. |
| Preparation, extraction process, method | Take pure clear yellow gelatin from market and pulverized into powder. |
| Effective ingredient | Collagen in the leather of the yellow ox is not soluble in water. Boiling with water for a long period can transform collagen into water soluble yellow gelatin. It contains nitrogen, sugar, multiple vitamins and helpful to plant growth. |
| Original recorded pharmacological effects | |

-continued

| NO: 9 Emulsifying agent | |
|---|---|
| Pharmacological applications, purposes | Promote growth of plants. It is used as emulsifying agent in this invention. |

| NO: 10 Agumenter | | | |
|---|---|---|---|
| Name | Puxiao | Official name | Mirabilite |
| Dependence | China Pharmacopoeia Volume I pp 269 (China Shang-Ghai scientific technology publication) | | |
| Growing district, collect season, parts | | | |
| Preparation, extraction process, method | Purchase authentic Mirabilite for later use. | | |
| Effective ingredient | Hydrated sodium sulfate (Na2SO4-10H2O) mainly with trace sodium chloride and inorganic elements such as calcium, magnesium and potassium. Use it to penetrate and soften. | | |
| Original recorded pharmacological effects | | | |
| Pharmacological applications, purposes | To produce cooperative or additional effect with drugs such as *Aloe vera*, *Gleditsia sinensis*, *Brucea javanica* and vice versa. It can promote pesticide, germicide and penetration effects. | | |

Field experiment example I Notolophus *Australia posticus, Chlorita flavescens* and tea red spider in tea tree farm.

| | |
|---|---|
| Objective of experiment | The effect of this invention is applied to the pest in the tree farm. |
| Time and place | Apr. 13, 2003. #1123 in Xin-kai Section, Liu-gui, Kaohsiung county. |
| Environment | There are 20 acres of dry land with elevation of 800 meters. Tea trees grow in 1983 then betel trees in 1990. |
| Status of pest damage | 1. Many diverse of tea trees and back of old leaves found larva of red spiders and some old leaves fallen.<br>2. The fresh leaves have bite wounds. Shaking the bush and found *Chlorita flavescens* flying everywhere. The situation is getting worse.<br>3. The down-left area of this tea tree farm appear larva of *Notolophus Australia posticus*. |
| Pest name and brief description | 1. Tea red spider is called tea mite. It's very tiny. The female is ellipse shaped and length is 0.34 mm. The male one is small shield shaped. The color is purple-red or deep red. The color in the back is faint. There are loose white fine hairs in the body. The legs are pale-red color. The larvas have 3 pairs of les and the adult has 4 pairs of legs. They damage old tea tree leaves and make them wither and fall.<br>2. *Chlorita flavescens* is called tea cicada. It is fragile. The body length is 1 to 3 mm with pale green and transparent body. The fore-wing is yellow only. They suck the juice of fresh leaves and block the development of tea tree leaves. The damages leaves are shrinking with faint-yellow color and the rim of leaves become brown. The leaves scroll into ship shape and fallen.<br>3. *Notolophus Australia posticus* is called red-head poison caterpillar or stinky dog. The body length is 22 to 30 mm. The body color is variable depend on seasons. In summer, the head is red and the body is in light yellow. There are may yellow and white long hairs all over the worm body. It will cause allergic itch and pain as touched human skin. They eat leaves of tea trees and damage severely in March to May. |
| General status of application | Use 100 times of water with 1 part of this preparation. Apply it with mobile sprayer. There are about 2000 tea trees. The original solution of this preparation used is 3 liters and 157 liters of water. |
| Effect evaluation | Inspect at afternoon of Apr. 14, 2004. There are no tea mites found and no *Chlorita flavescens* flying as shaking bushes. The *Notolophus Australia posticus* died in the ground. Inspect at afternoon of Apr. 20, 2004. The shoots of tea trees grow normally and no pests seen. |
| postscript | Actually, from the beginning of this tea tree farm opened. I always using Chinese medicine powder to dilute 150 times and proved effective. Now, I improved it into emulsion and dilute into 100 times and the effect more apparently. |

Field experiment example II *Pesudaulacaspis pentagonai* in magnolia tree.

| | |
|---|---|
| Objective of experiment | The effects of this invention apply to the *Pesudaulacaspis pentagonai* in magnolia tree. |
| Time and place | Nov. 24, 2003. #1123 in Xin-kai Section, Liu-qui, Kaohsiung county. |
| Environment | The magnolia tree is 20 years old and grew in front of the house. |
| Status of pest damage | There are 2 magnolia trees in these experiments. They have damaged by *Pesudaulacaspis pentagonai* for many years. The middle sections of the stem always show gray-white appearance. This appearance may extend to the |

-continued

| | |
|---|---|
| | twig and make the upper part green leaves of the damaged section withering. The blooms are weak and small. The twigs died at last. The trees is so big and good drainage and fresh air make them live till today. I can fell the humidity of larva and odor as touch the surface of the stem with hands. |
| Pest name and brief description | *Pesudaulacaspis pentagonai* Targioni-Tozzett is hosted on *Melia azedarach*, prune, plum, peach, almond tree, apple tree, magnolia tree and *Hibiiscus mutabilis*. The worms attach itself on the base of the stems first. The damages skin form gray-white or powder like sign. The larva and female suck juice and extend to the tip of twigs. The damaged twigs withering, drying and falling. The male is 0.75 mm in length with red color and its head is brown. It possesses antennas. The proboscis is degenerate and a pair of transparent wings on it. The legs are slender and the coupler is in needle shape. The female adult one is 1.3 mm in length. The body is hidden under the flat or slightly round gray-white shell with pale red-orange color. She has no antennas and wings. The proboscis is very sophisticated. The shell is round or short ellipse in white of gray-white color. The center has an umbilical spot. The diameter is 1.8 to 2.5 mm. The larva is flat and elliptic with pale yellow color. They secret shell and live under it after one exuviate. Proboscis |
| General status of application | Use 30 times of water with 1 part of this preparation. Apply it with mobile sprayer evenly on the gray-white twigs till all twigs are wetted. |
| Effect evaluation | I fell the stem damaged by pests were dry after 7 days of application. There are no pests and odor. After 14 days, The gray-white shells falling gradually. The upper part leaves of pest damaged are turning green. |
| postscript | |

Field experiment example III Aphids in *Solanum nigrum*.

| | |
|---|---|
| Objective of experiment | The effect of this invention is applied to the Aphids in *Solanum nigrum*. |
| Time and place | Nov. 17, 2003. #1123 in Xin-kai Section, Liu-qui, Kaohsiung county. |
| Environment | Left part of the house grows *Eapatorium fortunei*, Eapatorium Chinese and *Solanum nigrum*. |

-continued

| | |
|---|---|
| Status of pest damage | The *Solanum nigrum* are about 30. The twigs and leaves have transparent Aphids stay on it. The leaves curled and development retarded. |
| Pest name and brief description | Aphids have many species. They all belong to Order homoptera, Family Aphididae. The body length smaller than 3 mm. they always gather together to feed on leaved and fresh shoots or hide under recesses of fruits. The damage by group suction. The Aphids excrete honey droplets and we can see ants and coal dip as plants damaged by Aphids. That is the general identification knowledge of Aphids damage. |
| General status of application | Use 30 times of water with 1 part of this preparation. Apply it with mobile sprayer on all twigs. |
| Effect evaluation | Inspect in Nov 23, 2003. There are no trace of Aphids on the stems and leaves of *Solanum nigrum*. The curled leaves show some extend. There are coal dips on the leaves but no Aphids seen. |
| postscript | The inventor practice Chinese medicine in Gang-shan town as a physician. He will back to Liu-qui by afternoon Sunday regularly and back to Gang-shan at Monday. The evaluation must performed at Nov 23 because of the Nov 17 is Monday by himself. |

Field Experiment Example IV Ring Spot Virus Disease

| | |
|---|---|
| Objective of experiment | The effect of this invention is applied to the sick plants infected by ring spot virus. |
| Time and place | Nov. 02, 2003. #1123 in Xin-kai Section, Liu-qui, Kaohsiung county. |
| Environment | In front of the house. |
| Status of pest damage | The original developed normally Papaya trees had bloomed in August and September. In October, its inner leaves (Newly grow top leaves) appeared dotted line yellow spots. The yellowish shrink and the veins of leaves shown green stripes with apparent etched stripes. The development is retarded. |
| Pest name and brief description | Ring spot virus of Papaya tree is belonging to virus disease. It is different from pest and germ damages. It is appeared first time in Yan-cao, Kaohsiung county in 1975 and spread all over the province in 1 to 2 years. It is called "wild plant". It is spread by winged Aphids and machine recorded by agricultural experts. The features of this disease are the center leaves become yellow and shrink. The veins of leave are striped with vivid etched stripes. The sick leaves are |

-continued

| | |
|---|---|
| | smaller than normal leaves. The rim of leaves dried gradually and leaves fall. Only top survive or fall totally and cause death. The sick plants appear oil soaked spots or stripes in petioles and stems. The plants have small short petioles. There are oil soaked spots and stripes on the petals. Usually bloom but do not fruit. The fruits appear round or elliptic ring stripes. The sick plant can fruit continuously and the sick fruits lose value of merchandise or usage of application. |
| General status of application | Use 30 times of water with 1 part of this preparation. Apply it with mobile sprayer on all twigs. |
| Effect evaluation | Seven days after spray, There are no apparent differences between these 2 areas. After 14 days, The sick leaves shown brown spots. After 30 days, The new grow central leaves of south area appear striped yellow spots and the leaves look weak and wither. The central leaves of north area appear normal green color and the leaves look strong and prosper. The lower layer of developing leaves appear normal but the control group is withering and yellow. |
| postscript | The ring spot virus disease in Taiwan has been propagated for near 30 years. There is no effective drugs appear. They have no choice to use net house to culture them. The loss of annual agriculture is very huge. This appear of this invention is vividly a great Evangel. It needs to spray 3 to 4 times per year. |

Field experiment example V prevention of lima bean fruit fly.

| | |
|---|---|
| Objective of experiment | The effect of this invention is applied to the lima bean fruit fly. |
| Time and place | Nov. 09, 2003. #1123 in Xin-kai Section, Liu-qui, Kaohsiung county |
| Environment | Tented net style. The area is about 7 square meters. I plant 2 lima beans and fertile and irrigation as usual. The leaves and stems have spread on the net all. It is the period of bloom and fruiting. |
| Status of pest damage | The fresh bean capsule appear soften and falling phenomenon. There are bite trace near the head of the fresh buds. Yellow-white larva in the capsules after ripping the outer skin. The beans have the bite appearance. Some insects loitering and flying during white flower of bean bloom. |

-continued

| | |
|---|---|
| Pest name and brief description | The adult is larger than oriental fruit fly. By consulting the agricultural pest control data, identified as Daus cucrbitae Coeuilltt. It is belong to order Diptera, family Tephritidae. The main host plants are melon or tomato and Legurninosae. The color of the adult is yellow-brown. Body length is 8 to 14 mm with red-yellow legs and big wings. It looks like bee or fly. The purpose of this fly jumping between flowers is to increase its reproductive ability. It place eggs Insert into fruits. The larva hatched and feed in the fruits. The damaged fruits change shapes, falling or stop growing. The larva falls to the ground and make cocoon to reproduce. |
| General status of application | Use 30 times of water with 1 part of this preparation. Apply it with mobile sprayer on all stems and leaves and wetted them all then spray on the ground. |
| Effect evaluation | Some fruit flies fly away during spray. Some of them dropped and loss of flying ability. And die after 2 to 4 hours. There are no fruit flies flying observed in Nov 16, 2003. Some survived lima beams can harvest. |
| postscript | Inspect in Nov. 25, 2003. There are some fruit flies appear again. You need to spray every 2 weeks and have to spray onto the ground to make the cocoons of fruit flies loss of opportunities for reproduction. |

Field Experiment Example I (Comparison of Transformation)

| | |
|---|---|
| Objective of experiment | Comparison of pest killing effects on preparation (1) no emulsion, (2) emulsion. |
| Time and place | DEC. 14, 2003. #62 Sho-hwa Road, Gang-shan, Kaohsiung county in laboratory. |

-continued

| | |
|---|---|
| Pest sampling | Taking larva of *Piens rapae* Cruciuora Boisdurol from cabbage of private experiment garden and larva of *Hellula rogatalis* from *Cassia obtusifolia*. They are healthy worms. |
| Brief description of pest | *Piens rapae* Cruciuora Boisdurol is called green worm. The larva with green head and fine hairs on the body. Body length is about 2.5 to 3 cm. They feed on leaves and leave cores. You can found large quantities of feces in the base of leaves in the damaged plants. *Hellula rogatalis* is called vegetable worm or bean worm. The larva is 2 to 2.5 cm in length with black-brown head. Its body is green with annular rings and three white longitudal line and thick gray line in both body sides. They feed on leaves until petioles left. There are feces and silk strings between leaves. Those who digging into the core leaves of Cruciferae plants or cabbages and feed on it are in third stage larva. |
| Pre-experiment | Put test larva on filtering papers to avoid soaking. Using small hand sprayer to spray 3 times from left to right, right to left and far to near, all focus as the worms as the center. Then move the worms and filtering papers in to glass cabin for observation. |
| Experiment procedure | 1. This invention can be divided into no emulsion (1) and emulsion (2).<br>2. Then dilute it into 6 parts such as 5:1, 10:1, 15:1, 20:1, 25:1 and 30:1, respectively.<br>3. Take 6 *Hellula rogatalis* and 4 *Piens rapae* Cruciuora Boisdurol to perform experiment.<br>4. Observe time for result is 2 minutes after spray and 180 minutes, respectively. |
| Description and conclusion | 1. Depend on pharmacology and many results recorded from experiments. They show in situ movement only or stop moving in 2 minutes and I can not make sure they are death. The reason could be the paralysis effects of drugs or drugs can not penetrate into worm bodies. It is possible for them to re-vital in 30 to 60 minutes. I must make sure that they stop moving after 2 hours and realize that they are dead. For prudently, I determine it after 3 hours.<br>2. The difference between (1) and (2) is on the emulsion. The ingredients and adjuvant are the same.<br>3. Under 5:1 dilution ratio, stop moving (in 2 minutes) in preparation 1 are count 10 and preparation 2 show in situ movement of secondary potency. This is because of preparation 2 has added emulsion and the solution is too thick. The drug content is enough so 180 minutes left there are no crawling worms. The in situ movement worms show fatigue and gradually go to death.<br>4. Observe the situation and changes under dilution 15:1 and 30:1, we can find that worms' number in situ movement and crawling in preparation 1 are increasing. The in situ movement one do not show fatigue and will re-vital again. On the contrary, 2 worms in the 30:1 after 180 minutes in preparation 2 are all dead.<br>5. From the list shown above. Emulsified Chinese medicine herbal pest and germ killing preparation can increase 6 times of potency indeed.<br>6. Prepared by emulsion can enhance the potency of Chinese medicine herbs and it is the important feature of this invention. It is a new invention. |

Experiment list (*Hellula rogatalis*, *Piens rapae Cruciuora Boisdurol*)

| Dilution ratio | Worm body status | (1)No emulsion 1(in 2 mins) | (1)No emulsion 2(after 180 mins) | (2)Emulsion 1(in 2 mins) | (2)Emulsion 2(after 180 mins) |
|---|---|---|---|---|---|
| 5:1 | Stop moving | 10 | 6 | 0 | 8 |
| | In situ movement | 0 | 4 | 10 | 2 |
| | Crawling | 0 | 0 | 0 | 0 |
| 10:1 | Stop moving | 5 | 3 | 4 | 10 |
| | In situ movement | 5 | 7 | 6 | 0 |
| | Crawling | 0 | 0 | 0 | 0 |
| 15:1 | Stop moving | 5 | 3 | 10 | 10 |
| | In situ movement | 5 | 7 | 0 | 0 |
| | Crawling | 0 | 0 | 0 | 0 |
| 20:1 | Stop moving | 0 | 2 | 10 | 10 |
| | In situ movement | 10 | 8 | 0 | 0 |
| | Crawling | 0 | 0 | 0 | 0 |
| 25:1 | Stop moving | 0 | 0 | 10 | 10 |
| | In situ movement | 10 | 5 | 0 | 0 |
| | Crawling | 0 | 5 | 0 | 0 |

-continued

| Experiment list (*Hellula rogatalis*, *Piens rapae Cruciuora Boisdurol*) | | | | | |
|---|---|---|---|---|---|
| | Worm | (1)No emulsion | | (2)Emulsion | |
| Dilution ratio | body status | 1(in 2 mins) | 2(after 180 mins) | 1(in 2 mins) | 2(after 180 mins) |
| 30:1 | Stop moving | 0 | 0 | 8 | 10 |
| | In situ movement | 10 | 3 | 2 | 0 |
| | Crawling | 0 | 7 | 0 | 0 |

p.s.: Stop moving: There are 2 situations of paralysis fake death and death. Death means stop moving after 180 minutes.
In situ movement: It means the worm do not move everywhere but still alive as touch it by probe. We need to observe it is fatigue or not after 180 minute in situ movement. The fatigue one will die.
Crawling: It means the worm still has the ability to crawling.

Interior Experiment Example II (Eradiation of *Plutella xylostella*)

| | |
|---|---|
| Objective of experiment | The effect of killing *Plutella xylostella* in diluted emulsified preparation. |
| Time and place | Nov. 29, 2003. #62 Sho-hwa Road, Gang-shan, Kaohsiung county in laboratory. |
| Pest sampling | Pests were taken from Chiang-chi, Ping-dung county by working staff from coleseed shoots in glass greenhouse. |
| Brief description of pest | *Plutella xylostella* L. is called silk-hanging worm. It is belong to order Lepidoptera, family Plutellidae. The larva all hosted in Cruciferae. It likes cabbage, Broccoli, Chinese radish and coleseed. The usual larva is in the third or fourth stage and body length is under 1.3 cm. The color is green or kahki with apparent segmentation. It will fall upon stirring. It use silk to connect leaves and hanging in the air and is called silk-hanging worm. The larva digging into leaves and feed on it then moving to back of leaves after the second stage and make leaves broken. When the plants are small, they always gather together in the central leaves and spit silk to protect them and make plants can not sprout and causing death. This worm can have 20 generations in a year and possess extraordinary reproductive ability. |
| Pre-experiment | Put test larva on filtering papers to avoid soaking. Using small hand sprayer to spray 3 times from left to right, right to left and far to near, all focus as the worms as the center. Then move the worms and filtering papers in to glass cabin for observation. |
| Experiment procedure | 1. This preparation is dilute into 15:1, 20:1, 25:1, 30:1, and 40:1, respectively. 2. Choose same size 10 *Plutella xylostella* for testing. |
| Description and conclusion | The worms die with head bending backward and shaking. Observe after 180 minutes and found the middle section of worm bodies show dark green or black. I can make sure that all worms are killed with dilution ratio 15:1 to 30:1. There are 2 worms still have residue life in dilution ratio 40:1. |

Experiment List of *Plutella xylostella* (Silk-hanging worm)

| Dilution ratio | Worm body status | 1(in 2 mins) | 2(after 180 mins) |
|---|---|---|---|
| 15:1 | Stop moving | 10 | 10 |
| | In situ | 0 | 0 |
| | Crawling | 0 | 0 |
| 20:1 | Stop moving | 10 | 10 |
| | In situ | 0 | 0 |
| | Crawling | 0 | 0 |
| 25:1 | Stop moving | 10 | 10 |
| | In situ | 0 | 0 |
| | Crawling | 0 | 0 |
| 30:1 | Stop moving | 8 | 10 |
| | In situ | 1 | 0 |
| | Crawling | 1 | 0 |
| 40:1 | Stop moving | 6 | 8 |
| | In situ | 2 | 2 |
| | Crawling | 2 | 0 |

Interior Experiment Example III (Eradiation of *Oebia undalis*)

| | |
|---|---|
| Objective of experiment | The effect of killing *Plutella xylostella* in diluted emulsified preparation. |
| Time and place | Dec. 07, 2003. #1 Cha-shen Road, Liu-qui, Kaohsiung county. |

-continued

| | |
|---|---|
| Pest sampling | From farmer Mr. jia-mow, Ho. |
| Brief description of pest | *Oebia undalis* Fabriciu S. is called "vegetable worm", "vegetable core worm", "radish worm" and "core-drilling worm". It is belong to order Lepidoptera, family Pyralidae. The larva damage radish severely in Taiwan. It also damages other plants of Cruciferae. It will dig into core leaves and feed on it and also turn into stems or over-ground roots. Drilling many hole in it. You can see many feces accumulated outside these pores. Ripping the damages parts and found larva about 0.8 cm in length with black head. There are 5 longitudal lines from foreside to the tail. The adult is about 1 cm in length. |
| Pre-experiment | Put test worm on wrapping papers and use small hand sprayer to spray 3 times from left to right, right to left and far to near. Let the table incline immediately to avoid soaking. Observe within 2 minutes and remove worms into ventilated plastic bottles and place some clean and fresh leaves. |
| Experiment procedure | 1. This preparation is dilute into 15:1, 20:1, 25:1, 30:1, and 40:1, respectively. 2. Choose same size 10 *Plutella xylostella* for testing. |
| Description and conclusion | After 180 minutes, there are still 1 to 2 worms can crawling with dilution 25:1 and 30:1. It is obvious that the *Oebia undalis* is more resistant than *Piens rapae* Cruciuora and *Plutella xylostella*. |

Experiment List of *Oebia undalis* (Core-Drilling Worm)

| Dilution ratio | Worm body status | 1(in 2 mins) | 2(after 180 mins) |
|---|---|---|---|
| 10:1 | Stop moving | 10 | 10 |
| | In situ | 0 | 0 |
| | Crawling | 0 | 0 |
| 15:1 | Stop moving | 10 | 10 |
| | In situ | 0 | 0 |
| | Crawling | 0 | 0 |
| 25:1 | Stop moving | 8 | 9 |
| | In situ | 2 | 1 |
| | Crawling | 0 | 0 |
| 30:1 | Stop moving | 5 | 4 |
| | In situ | 3 | 4 |
| | Crawling | 2 | 2 |

Interior Experiment Example VI (Eradiation of *Plutella xylostella* and *Piens rapae*)

| | | |
|---|---|---|
| Objective of experiment | To test the prevention effect of this preparation and effect o growth of plants. | |
| Time and place | Plant in Oct. 27, 2003 in #0148-0048 Wan-tze-nei section, Gang-shen town | |
| Experiment design | By normal plant methods, divide into A, B and C areas. Each area plant 20 cabbages. The area A is the experiment area and Areas B and C are control. The fertilizing and irrigation are as the usual ways. | |
| Implementation procedure | Plant cabbage shoots in Oct. 27, 2003. | |
| | Nov 3 | Spray area A in 30:1 dilution ratio with manual sprayer. The controls do not spray. |
| | Nov 10 | Area A does not show sign of worm damage and no eggs found. Today do not spray. The control areas found 6 *Plutella xylostella* and some eggs. |
| | Nov 17 | Area A has 1 plant damaged by worm. One *Piens rapae* found. Spray with 30:1 solution. The control areas found 3 *Piens rapae* and 4 *Plutella xylostella*. |
| | Nov 24 | Area A does not show sign of worm damage and no worms found. Today do not spray. The control areas found 2 *Piens rapae* and 6 *Plutella xylostella*. |
| | Dec 1 | Area A does not show sign of worm damage. Spray with 50:1 solution. The control areas found 2 *Piens rapae* and 8 *Plutella xylostella*. |
| | Dec 8 | Area A does not show sign of worm damage and no worms found. Today do not spray. The control areas found 3 *Piens rapae* and 6 *Plutella xylostella*. |
| | Dec 15 | Area A does not show sign of worm damage. Spray with 60:1 solution. Today do not spray. The control areas found 2 *Piens rapae* and 4 *Plutella xylostella*. |
| | Dec 29 | Area A does not show sign of worm damage and no worms found. The control areas found 6 *Piens rapae* and 4 *Plutella xylostella*. |
| Effect evaluation | 1. Spray area A every 14 days. I grab 1 green worm in Nov 17 and there are no damage till Dec. 29, 2003 2. The dilution ratio in spray gradually increased from 30 to 60:1 and the dosage decrease still effective. 3. The cabbage is ripped at Dec. 29, 2003. The growth status show no difference but the controls have 4 plants with bad formation. | |

What is claimed is:

1. A Chinese medicine composite recipe used in horticulture as a pesticide comprising the ingredients *Gleditsia sinensis, Sophora flavescens, Stemona tuberosa, Brucea javanica*, and *Mirabilite*, wherein said Chinese medicine composite recipe is prepared by dissolving the ingredients in emulsifying agents.

2. The Chinese medicine composite recipe as defined in claim 1, wherein said emulsifying agent comprises turpentine oil and Mosla chinensis oil and one of Colla corii Bon's or gum Arabic.

3. The Chinese medicine composite recipe as defined in claim 2 wherein said Mosla chinensis oil consists essentially of thymol, carvacrol, and p-cymene.

4. The Chinese medicine composite recipe as defined in claim 3 further comprising *Aloe vera.*

5. The Chinese medicine composite recipe as defined in claim 4 further comprising pesticidal *Dioscorea collettii* as adjuvant.

6. A horticultural pesticidal agent having a solution and an emulsifying agent, wherein every 3000 ml of said solution in component proportion comprises Chinese medicine fine powders of *Gleditsia sinensis* 80-120 gm, *Sophora flavescens* 80-120 gm, *Stemona tuberosa* 100-140 gm, *Brucea javanica* 100-140 gm and *Mirabilite* 30-120 gm.

7. The horticultural pesticidal agent as defined in claim 6 further comprising *Aloe vera* 60-100 gm.

8. The horticultural pesticidal agent as defined in claim 6, wherein said emulsifying agent comprises turpentine oil 40-60 ml, Mosla chinensis oil 30-50 ml and one of Colla corii Bon's or gum Arabic 40-60 gm.

* * * * *